United States Patent
Boyce

(10) Patent No.: US 7,726,319 B1
(45) Date of Patent: Jun. 1, 2010

(54) METHOD FOR REMOVAL OF WATER ASSOCIATED WITH BONE WHILE DIMINISHING THE DIMENSIONAL CHANGES ASSOCIATED WITH LYOPHILIZATION

(75) Inventor: Todd M. Boyce, Aberdeen, NJ (US)

(73) Assignee: Osteotech, Inc., Eatontown, NJ (US)

( * ) Notice: Subject to any disclaimer, the term of this patent is extended or adjusted under 35 U.S.C. 154(b) by 1310 days.

(21) Appl. No.: 09/644,614

(22) Filed: Aug. 24, 2000

(51) Int. Cl.
*A61B 19/00* (2006.01)

(52) U.S. Cl. .................. 128/898; 623/919; 623/923; 623/16.11

(58) Field of Classification Search ............ 623/16.11, 623/66, 919, 923; 606/55, 76; 600/36; 128/898; 424/423; 523/115, 113
See application file for complete search history.

(56) References Cited

U.S. PATENT DOCUMENTS

| | | | |
|---|---|---|---|
| 4,277,238 A | 7/1981 | Katagiri | |
| 4,656,047 A | 4/1987 | Kok et al. | |
| 5,073,373 A | 12/1991 | O'Leary et al. | |
| 5,264,214 A | 11/1993 | Rhee et al. | |
| 5,290,558 A | 3/1994 | O'Leary et al. | |
| 5,314,476 A | 5/1994 | Prewett et al. | |
| 5,324,775 A | 6/1994 | Rhee et al. | |
| 5,507,813 A | 4/1996 | Dowd et al. | |
| 5,513,662 A | 5/1996 | Morse et al. | |
| 5,531,791 A | 7/1996 | Wolfinbarger, Jr. | |
| 5,725,579 A * | 3/1998 | Fages et al. ................. 128/898 |
| 5,776,193 A | 7/1998 | Kwan et al. | |
| 5,788,941 A * | 8/1998 | Dalmasso et al. ............. 422/33 |
| 5,797,871 A * | 8/1998 | Wolfinbarger, Jr. .......... 128/898 |
| 5,820,581 A * | 10/1998 | Wolfinbarger, Jr. .......... 128/898 |
| 5,846,484 A | 12/1998 | Scarborough et al. | |
| 5,862,806 A | 1/1999 | Cheung | |
| 5,899,939 A | 5/1999 | Boyce et al. | |
| 5,906,827 A * | 5/1999 | Khouri et al. ................ 424/423 |
| 5,976,104 A * | 11/1999 | Wolfinbarger, Jr. .......... 128/898 |
| 5,977,432 A * | 11/1999 | Wolfinbarger et al. ....... 128/898 |
| 6,025,538 A | 2/2000 | Yaccarino, III | |
| 6,110,482 A * | 8/2000 | Khouri et al. ................ 424/423 |
| 6,162,258 A | 12/2000 | Scarborough et al. | |
| 6,217,614 B1 * | 4/2001 | Fages et al. .............. 623/16.11 |
| 6,305,379 B1 * | 10/2001 | Wolfinbarger, Jr. .......... 128/898 |

FOREIGN PATENT DOCUMENTS

| WO | 95/19797 | 7/1995 |
|---|---|---|
| WO | 99/51170 | 10/1999 |

(Continued)

OTHER PUBLICATIONS

Carson, F. Histotechnology, A Self-Instructional Text (Date Unknown), ASCP Press, pp. 25-35.

(Continued)

*Primary Examiner*—William H. Matthews
(74) *Attorney, Agent, or Firm*—Kenneth E. Levitt; Dorsey & Whitney LLP

(57) ABSTRACT

A method for dehydrating a monolithic bone intended for implantation is provided. The method serves to conserve at least one of the biomechanical properties of the bone during the dehydration of the bone and its subsequent packaging. Also provided is a monolithic bone for implantation and a method of using the bone for the repair of damaged bone.

17 Claims, 4 Drawing Sheets

FOREIGN PATENT DOCUMENTS

WO 99/66967 12/1999

OTHER PUBLICATIONS

Boyne, P., Cryobiology, vol. 4, No. 6 (1968), pp. 341-357.
Pappas, A., Cryobiology, vol. 4, No. 6 (1968), pp. 358-375.
Reddi, et al. Proceedings National Academy Science USA, vol. 69, No. 6 (1972) pp. 1601-1605.
Triantafyllou et al., Acta Orthopaedica Belgica, vol. 41, Suppl. I (1975), pp. 35-44.
Pelker, et al., Clinical Orthopaedics and Related Research, No. 174 (Apr. 1983), pp. 54-57.
Pelker et al., Journal of Orthopaedic Research, vol, 1, No. 4 (1984), pp. 405-411.
Pelker et al., Orthopedic Clinics of North America, vol. 18, No. 2 (Apr. 1987), pp. 235-239.
Currey, J., Journal of Biomechanics, vol. 21, No. 5 (1988), pp. 439-441.
Jerosch et al., Zeitschrift Orthopädie 132 (1994), pp. 335-341.
Voggenreiter et al., Archives of Orthopaedic and Traumatic Surgery, vol. 113 (1994), pp. 294-296.
Kang et al., Yonsei Medical Journal, vol. 36, No. 4 (1995), pp. 332-335.
Bancroft et al., Theory and Practice of Histological Techniques, (1996), pp. 47-67.
Bianchi et al. 21$^{st}$ Annual Meeting, American Association of Tissue Banks (Aug. 23-27), p. 48.
Balderson et al., 45$^{th}$ Annual Meeting, Orthopaedic Research Society (Feb. 1-4, 1999), p. 785.

* cited by examiner

Scale: 10 = Highly Fragmented
1 = Intact (No Fragmentation)

Abbreviations:  Al. = Alcohol
Hy. = Hydration
VIP = Vacuum Infiltration Processor
S. = Sonicated
F.D. = Freeze-Dried

METHOD FOR REMOVAL OF WATER ASSOCIATED WITH BONE WHILE DIMINISHING THE DIMENSIONAL CHANGES ASSOCIATED WITH LYOPHILIZATION

BACKGROUND OF THE INVENTION

Bone grafting is widely used to treat fractures, non-unions and to induce arthrodeses. Autogenous cancellous bone, which is taken from one site in the graftee and implanted in another site of the graftee, is considered by many to be the most effective bone graft. Autogeneous cancellous bone provides the scaffolding to support distribution of the bone healing response. Autogeneous cancellous bone also provides the connective tissue progenitor cells which form new cartilage or bone. However, the harvest of autogenous bone results in significant cost and morbidity, including scars, blood loss, pain, prolonged operative and rehabilitation time and risk of infection. Furthermore, in some clinical settings, the volume of the graft required by the graft site can exceed the volume of the available autograft. Accordingly, alternatives to autografts have been developed in an attempt to reduce the morbidity and cost of bone grafting procedures.

The use of allograft bone or xenograft bone is well known in both human and veterinary medicine. See Stevenson et al., *Clinical Orthopedics and Related Research,* 323, pp. 66-75 (1996). In particular, transplanted bone is known to provide support, promote healing, fill bony cavities, separate bony elements such as vertebral bodies, promote fusion and stabilize the sites of fractures. More recently, processed bone has been developed into shapes for use in new surgical applications, or as new materials for implants that were historically made of non-biologically derived materials.

Because the use of preserved bone intended for implantation to replace diseased or missing parts is common, the successful application of such bone is predicated on sound knowledge of its biologic properties and its capacity to withstand the stresses to which it will be subjected. When mineralized bone is used in grafts, it is primarily because of its inherent strength, i.e., its load bearing ability at the recipient site. The biomechanical properties of bone grafts upon implantation are determined by many factors, including the specific site from which the bone is taken; the age, sex, and physical characteristics of the donor; and the method chosen to prepare, preserve, and store the bone prior to implantation. A more detailed explanation of the alteration of the biomechanical properties of bone by the methods chosen for its preservation and storage may be found in Pelker et al., *Clin. Orthop. Rel. Res.,* 174:54-57 (1983). However, the needs for processing (e.g., to preserve the graft for later use and to remove immunogenic cellular materials) can conflict with the need to conserve the toughness of the bone.

During the preparation of bone intended for implantation the porous matrix is typically contacted with one or more treatment fluids to variously clean, defat, sterilize, virally inactivate, disinfect, and/or demineralize the bone or to impregnate the bone with one or more pharmacological agents (antibiotics, bone growth factors, etc.) so the bone can act as a drug delivery system. See U.S. Pat. No. 5,846,484 for a detailed explanation of the treatment of bone intended for implantation. Some treatment processes, such as irradiation and lyophilization, can work against conservation of the mechanical properties of bone and can lessen the bone's weight bearing properties. Processing requirements can also create dimensional changes in the allograft bone. Such changes of dimension can create damage within the tissue, and may also make it difficult for a machined piece to mechanically engage with surgical instruments, other allografts, or the prepared surgical site. Treatment processes also can have a deleterious effect on such important mechanical properties as toughness. Implants demonstrating improved toughness are important as the insertion of some allografts can be quite energetic, e.g., the hammering in of cortical rings used in spinal fusion surgery.

Bone intended for implantation is currently distributed either frozen or lyophilized. It is generally accepted that freezing monolithic bone to temperatures as cold as −70° C. prior to its packaging and storage results in little if any alteration in its physical properties. However, freezing bone as a preservation technique is costly and can be logistically difficult, e.g., shipping and storage. Lyophilization (freeze-drying, i.e., freezing, then sublimation of moisture) is commonly performed on bone to permit its shelf storage for up to several years without spoilage.

Lyophilization removes excess moisture from the bone and reduces its antigenicity. According to the American Association of Tissue Banks ("A.A.T.B."), lyophilized whole bone containing no more than 6% moisture can be stored at ambient temperatures for up to five years after processing. However, adverse changes in the biomechanical properties of the bone have been found to result from the lyophilization procedure. Lyophilization can result in damage to the bone due to dimensional changes that occur during the freezing and dehydrating operations. The adverse mechanical changes appear to be associated with damage occurring in the bone matrix, specifically, ultrastructural cracks along the collagen fibers. These effects appear to be magnified when lyophilization and gamma irradiation are used together. Studies using rat bones to model the effects of lyophilization upon the compressive properties of cancellous bone (compression strength of tail vertebrae) and the bending and torsional properties of the long bones indicate that compressive strength can be reduced by up to 30% with little or no change in stiffness, bending strength can be reduced by as much as 40%, and torsional strength can be reduced by up to 60%. These changes, resulting in bone that is brittle, have been found to occur even after the bone has been rehydrated. A more detailed explanation of the effects of lyophilization on mineralized bone can be found in Kang et al., *Yonsei Med J* 36:332-335 (1995), and Pelker et al., *J. Orthop. Res.* 1:405-411 (1984).

Thus, a problem exists in providing a bone intended for implantation that is both tough and convenient to store and maintain. Because freezing and thawing bone is minimally damaging to the bone, whereas lyophilization results in reduction in the toughness of the bone, it is the inventors' belief that toughness is maintained and/or enhanced in the bone by dehydrating the bone using methods that remove the water associated with the bone while diminishing the dimensional changes associated with lyophilization. The dehydration of tissue, for example, by treatment with an anhydrous polar organic solvent such as ethanol, is known. See, for example, U.S. Pat. No. 5,862,806 to Cheung. However, it has not been previously appreciated that applying this technique to bone results in an implant having improved biomechanical properties, e.g., toughness. Thus, it is desirable to provide a method for dehydrating monolithic bone intended for implantation prior to its packaging and storage that will better conserve the biomechanical properties of the bone, i.e., its toughness and/or dimensions as compared to lyophilized bone, from the time the bone is harvested through the packaging and storage operations and to time of implantation.

SUMMARY OF THE INVENTION

It is therefore an object of the present invention to provide a method for dehydrating monolithic bone intended for implantation in order to conserve the biomechanical properties of the bone during its dehydration process and subsequent packaging and storage and to substantially maintain such biomechanical properties throughout its rehydration and subsequent implantation.

It is a further object of the invention to provide a method of dehydrating monolithic bone that reduces the dimensional change associated with the lyophilization of bone.

It is a further object of the invention to provide a method of dehydrating monolithic bone that improves the toughness of the bone graft.

It is a further object of the invention to provide a method of dehydrating monolithic bone with minimal negative impact to the biological properties of the bone graft.

It is a further object of the invention to provide a method for packaging dehydrated monolithic bone so that the bone may be stored at ambient temperatures for an extended period of time, e.g., up to five years or longer without excessive loss of its toughness.

It is a further object of the invention to provide a method for the rehydration of dehydrated monolithic bone such that the toughness of the bone at the time of its implantation is optimized.

It is a further object of the invention to provide a method that minimizes the tendency for a partially rehydrated graft to fracture due to the insertion forces applied by the surgeon.

It is a further object of the invention to provide a dehydrated monolithic bone implant optionally containing one or more medically/surgically useful substances, e.g., an osteogenic material such as bone morphogenic proteins (BMPs).

These and other objects not specifically set forth above will be apparent to those skilled in the art in view of the objects set forth above and the foregoing specification.

In keeping with these and related objectives of the invention, there is provided a method for dehydrating monolithic bone intended for implantation to conserve the biomechanical properties of the bone during the dehydration process and subsequent packaging and to maintain such biomechanical properties during the storage of the bone preceding its implantation. The method comprises:

dehydrating without lyophilizing the monolithic bone; and, packaging the dehydrated bone.

In another aspect, the invention includes the dehydrated bone obtained by the foregoing method(s) and use of bone obtained by the invention herein.

The expression "monolithic bone" as utilized herein refers to relatively large pieces of human or animal bone, i.e., pieces of bone, autograft, allograft or xenograft, that are of such size as to be capable of withstanding the sort of mechanical loads to which functioning bone is characteristically subjected. The monolithic bone of this invention is to be distinguished from particles, filaments, threads, etc. as disclosed in U.S. Pat. Nos. 5,073,373, 5,314,476 and 5,507,813, which, due to their relatively small dimensions, are incapable of sustaining significant mechanical loads, either individually or in the aggregate. It is further to be understood that the expression "monolithic bone" refers to fully mineralized bone, i.e., bone with its full natural level of mineral content, and to such bone that has been demineralized to some minor extent, i.e., to an extent which reduces the original strength of the bone by no more than about 50 percent. The monolithic bone can be provided as a single integral piece of bone or as a piece of bone permanently assembled from a number of smaller bone elements, e.g., as disclosed and claimed in U.S. Pat. No. 5,899,939 the contents of which are incorporated herein by reference. Although monolithic bone can contain factors which are osteogenic, monolithic bone can also contain additional materials, e.g., as disclosed in U.S. Pat. No. 5,290,558 the contents of which are incorporated herein by reference, which will remain with the bone after its rehydration and will be present at the time of implantation.

The expression "strength" as utilized herein is intended to mean any one of the principal biomechanical properties of bone, specifically including compression strength, flexural modulus, torsional modulus and yield strength, as well as the sum of these properties, that are characteristic of bone.

The expression "toughness" as utilized herein is intended to refer to any characteristic that qualitatively can be described as the way in which the bone fails, i.e., how the bone undergoes deformation prior to fracture. For example, bone that exhibits improvement in toughness would be more desirable than bone having less toughness. Quantitatively, "toughness", as utilized herein, is a measure of the energy absorbed by the osteoimplant prior to breakage and is expressed in units of force times length, such as Newton-millimeters (N-mm).

The expressions, "toughness-enhancing", "conserving the toughness of the bone" and expressions of like import shall be understood herein to mean that the monolithic bone dehydrated in accordance with the invention shall demonstrate at least greater than about 5% increase in toughness as compared to bone that has been lyophilized. That is, bone dehydrated in accordance with the invention herein will demonstrate improved ability to withstand the forces occurred during implantation as compared to bone that is lyophilized.

The expression "dimensional-conserving" and expressions of like import shall be understood herein to mean that the monolithic bone treated in accordance with the invention, shall demonstrate at least about 2% less decrease in length dimension as compared to bone that has been lyophilized. That is, bone dehydrated in accordance with the invention herein will demonstrate less shrinkage after dehydration than lyophilized bone.

The term "biocompatible" and expressions of like import shall be understood to mean the absence of stimulation of an undesired severe, long-lived or escalating biological response to an implant and is distinguished from a mild, transient inflammation which accompanies implantation of essentially all foreign objects into a living organism and is also associated with the normal healing response. Materials useful to the invention herein shall be considered to be biocompatible if, at the time of implantation, they are present in a sufficiently small concentration such that the above-defined condition is achieved.

DETAILED DESCRIPTION OF THE INVENTION

Figure 1:
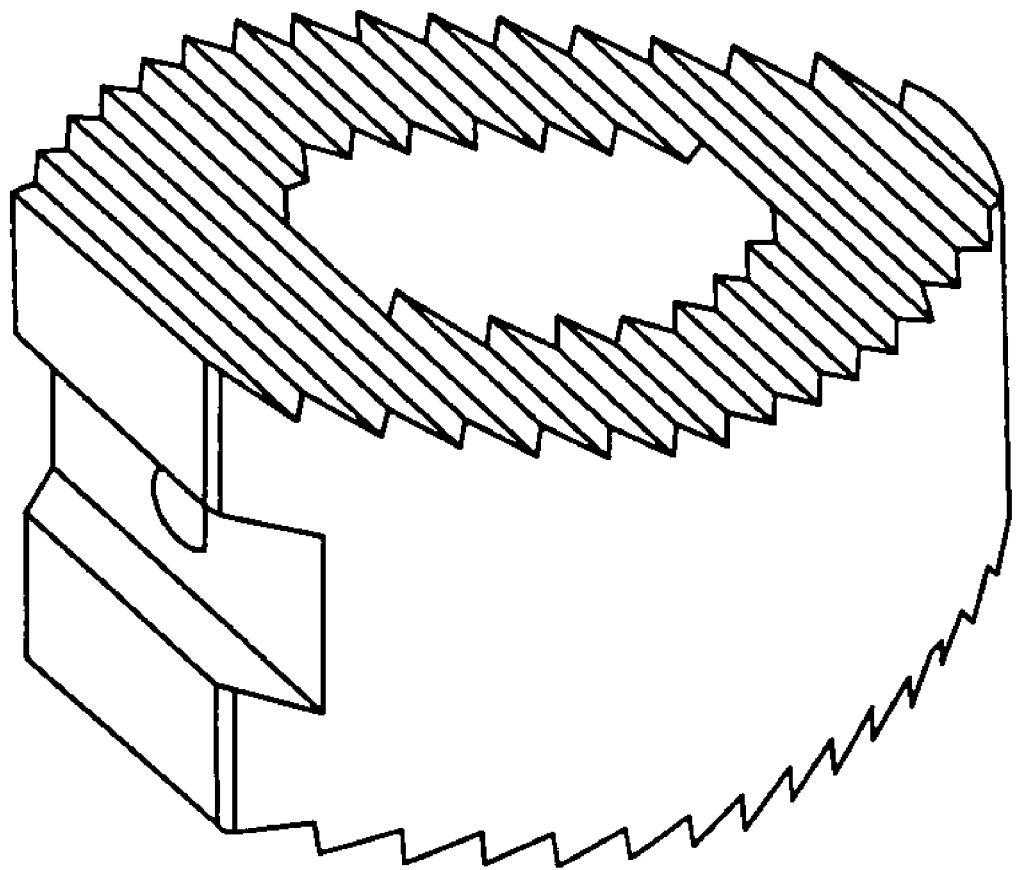
FIG. 1 represents the monolithic bone processed according to the invention herein.
Figure 2:
FIG. 2 is a photograph of a freeze-dried monolithic bone after it was subjected to compression to fracture.
Figure 3:
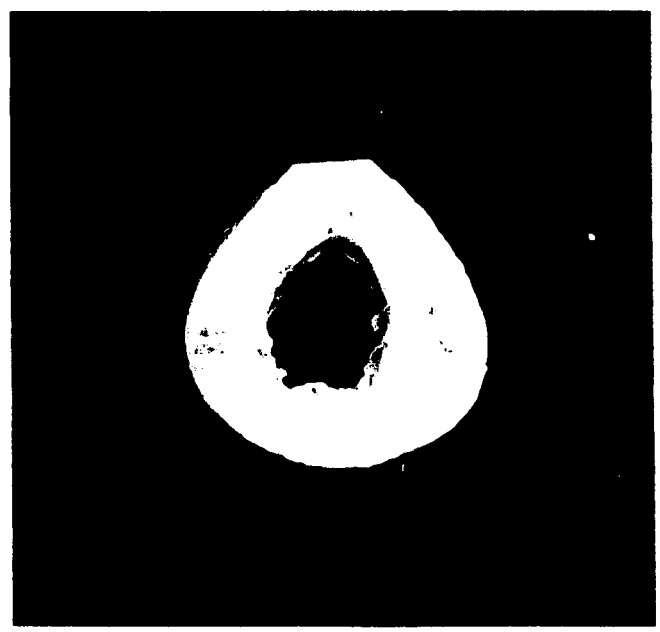
FIG. 3 is a photograph of a frozen monolithic bone after it was subjected to compression to fracture.
Figure 4:
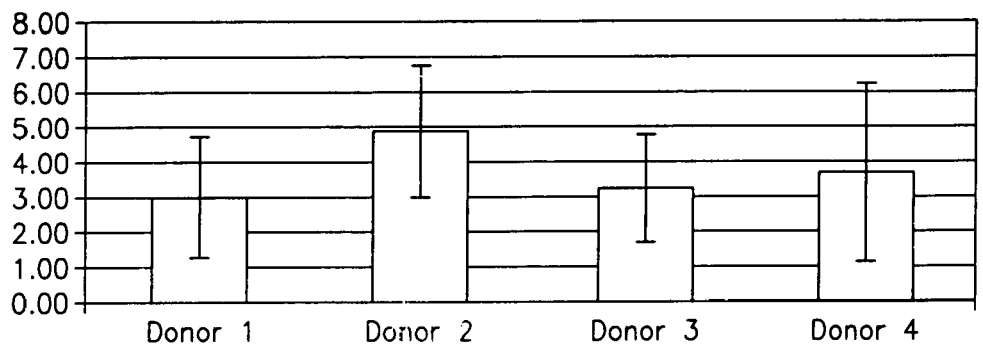
FIG. 4 is a graph of the average degree of fragmentation by donor.
Figure 5:
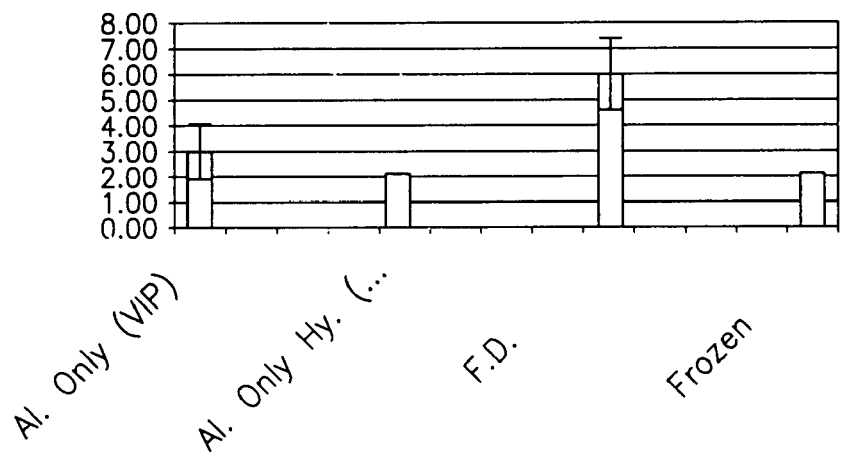
FIG. 5 is a graph of the average degree of fragmentation by treatment.
Figure 6:
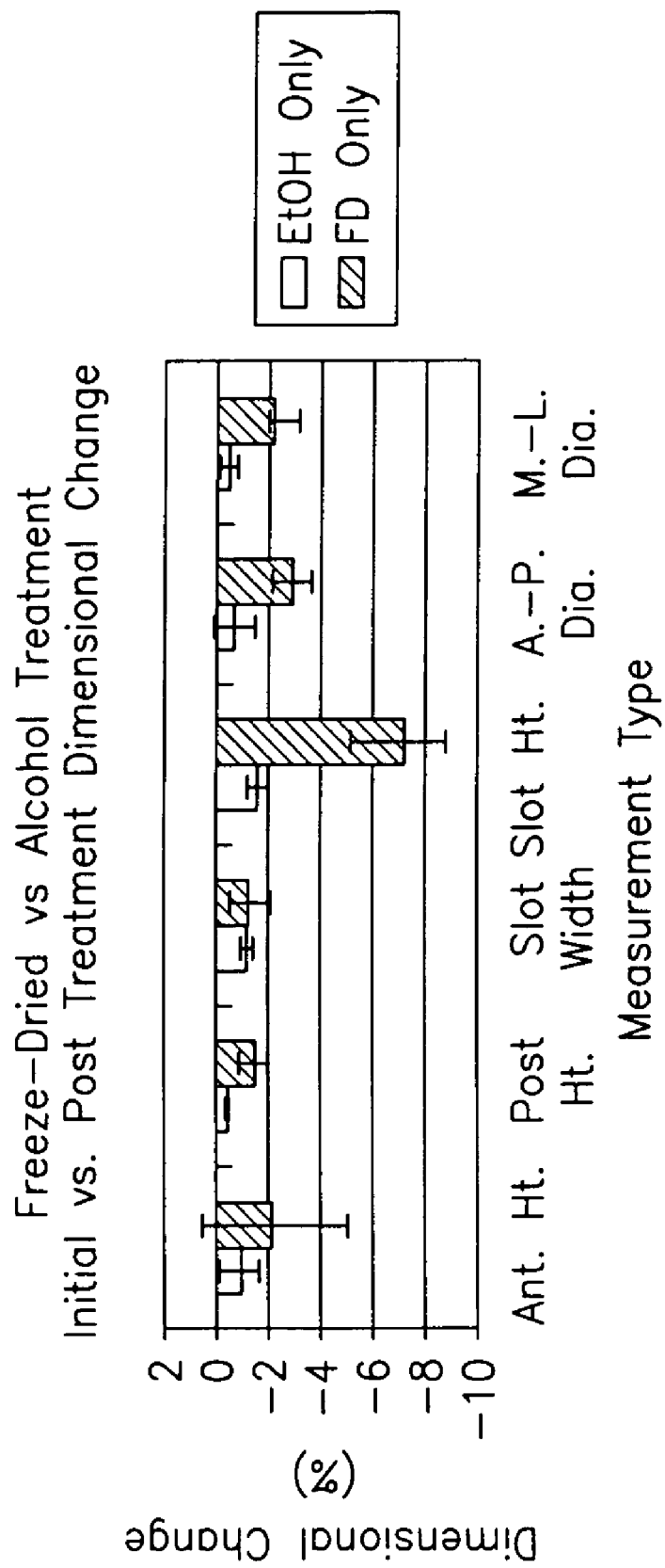
FIG. 6 is a graph of the percentage dimensional change by treatment.

Bone for implantation is obtained e.g., aseptically in a morgue or an operating room from a cadaver donor or from a living donor's tissue obtained by surgical excision or amputation. The bone is cleansed using, e.g., 70% ethanol and washed with water for injection and sonication. This use of alcohol in the initial processing of bone for implantation is common to the industry and may have some dehydrating effect. However, the dehydrating effect, if any, is negligible and would not bring the bone within the less than 6% water content required by the A.A.T.B. prior to storage of bone intended for implantation. The bone may be treated with antibiotics such as polymyxin B sulfate, bacitracin, and/or gentamicin, and may contain trace amounts of residual antibiotics. Cleansing, cutting, sizing, shaping, container sterilization, filling, dehydration, and stoppering functions may be performed under conditions following industry standards for tissue handling. The bone employed in the invention is of monolithic proportions in contrast to "particles," "filaments," "threads," "strips," etc., as described in U.S. Pat. Nos. 5,073,373, 5,314,476 and 5,507,813. Thus, the bone treated according to the method of the invention is generally a relatively large piece or segment of donor bone and is intended for implantation into a correspondingly relatively large defect or other implantation site. Typically, the bone herein will possess dimensions of length on the order of about 2 mm to about 500 mm and preferably at least about 5 mm to about 100 mm. Similarly, dimensions of width will be on the order of about 1 mm to about 600 mm and preferably at least about 1 mm to about 100 mm. Dimensions of thickness will be on the order of about 1 mm to about 30 mm and preferably at least about 1 mm to about 10 mm. Any one of several methods, including but not limited to, cutting, forming and machining can readily obtain such bone.

The expression "dehydrating liquid" as utilized herein is intended to refer to any suitable solvent or mixture of solvents having a vapor pressure at relevant temperature, i.e., the temperature at which dehydration takes place, such that the solvent is readily passed off by evaporation. Such dehydrating liquid(s) will be suitable even if ordinarily considered to be toxic so long as the amount of dehydrating liquid, if any, present at the time of implantation does not produce a toxic response. Examples of dehydrating liquids useful in the invention herein would include but not be limited to, polar organic solvents, e.g., alcohol, typically a low molecular weight alcohol such as methanol, ethanol, isopropanol, butanol, isobutanol, ethylbutanol, acetonitrile, pyridine, industrial methylated spirit, etc.; histological solution, e.g., Flex 100™; polar solvent, e.g., dimethylsulfoxide, small ketones, acetone; chloroform; methylene chloride and ethylene chloride; straight chain hydrocarbons, e.g., hexane, pentane and similar alkanes; low molecular weight alkenes; esters; ether, e.g., ethyl ether, tetrahydrofuran, dioxane, ethylene glycol monoethyl ether, crown ethers, etc.; aldehyde or solutions containing aldehydes, e.g., formaldehyde, formalin, etc., at low temperatures such that cross-linking does not proceed; super critical fluids, e.g., carbon dioxide or hydrogen sulfide at supercritical pressures, mixtures of any of the above liquids, etc. Such dehydrating liquids may be selected in accordance with the present virtue of their ability to extract water from the bone, while not reacting adversely with the bone. Such dehydrating liquids can preferably be present in a graded series of aqueous concentration, e.g., 60% ethanol, 70% ethanol, 95% ethanol, absolute ethanol, which serves to promote the removal of the water associated with the monolithic bone.

The dehydrating liquid should have a viscosity at 20° C. of no greater than about 1410 cps, preferably the viscosity is between about 2 and about 300 cps. The preferred dehydrating liquid is a series of graded dehydrating alcohols.

The bone is contacted with the dehydrating liquid in a suitable container, e.g., a 120 ml or 500 ml bottle, optionally with mechanical stirring. Optionally, the dehydrating liquid can be applied by infusing, e.g., employing a pressurized system such as that described in U.S. Pat. No. 5,846,484 the contents of which are incorporated herein by reference. Pretreatment of tissues using the process described in U.S. Pat. No. 5,846,484 or a process using varying levels of positive pressure can improve the speed at which the dehydrating liquid penetrates the tissue. Optionally, the dehydrating liquid can be contacted with the bone in the presence of a low pressure atmosphere such as that described in U.S. Pat. No. 5,513,662 the contents of which are incorporated herein by reference or in the low pressure atmosphere provided by vacuum packaging the bone and dehydrating liquid utilizing a vacuum sealer. Optionally, the dehydrating liquid can be contacted with the bone in the presence of alternating vacuum and positive pressure such as that provided by the Hypercenter™ XP Enclosed Tissue Processor commercially available from Shandon Lipshaw USA or preferably a Sakura Tissue-TEK® VIP 150™ vacuum infiltration tissue processor commercially available from Sakura FineTek, USA. As one skilled in the art will readily appreciate, the optimal times and levels of alternating vacuum-positive pressure or varying positive pressure can be determined through routine experimentation. The tissue processor allows for the dehydrating of the bone when preferably a graded series of dehydrating liquids is used.

To assist the dehydrating liquid in penetrating the small pores of the bone, the bone and dehydrating liquid can be advantageously subjected to sonication. It has been determined that contacting the bone with dehydrating liquid in an ultrasonic bath improves the penetration of the liquid into the tissue. Sonicating bone is well known in the art and is described in U.S. Pat. No. 5,797,871 the contents of which are incorporated herein by reference. Of course, it will be understood by one skilled in the art, that the contacting of the bone with the dehydrating liquid can be carried out by any combination of one or more of the foregoing.

After the bone has been in contact with the dehydrating liquid for a period of about 5 minutes to about 7 days, preferably at least about one hour, it can optionally be shaped prior to removal of the dehydrating liquid. Such shaping can be accomplished by cutting, forming, machining or other method of shaping bone. Thus, the bone can be rough cut, processed with dehydrating liquid, further shaped as desired, then subjected to further processing if necessary. Such shaping of bone intended for implantation is well known in the art and is described in U.S. Pat. No. 6,025,538, the contents of which are incorporated herein by reference.

After shaping or other optional processing steps, the bone intended for implantation may be further dehydrated following procedures well known in the art. For example, the bottle containing bone and dehydrating liquid is initially frozen to −76° C. with the bone and dehydrating liquid later being subjected to a vacuum of less than 100 millitorr while the temperature is maintained at or below −35° C. The end point of the procedure is the determination of residual moisture of approximately 6% or less. Once the bone has been dehydrated, it is stored in sealed, vacuum-contained, bottles prior to its reconstitution and use although, of course, any suitable packaging means, e.g., polymeric tray packages (inner and outer sealed trays), are entirely suitable and are envisioned as being within the scope of the invention herein.

Other methods of dehydrating and/or dehydrating liquid removal would include but not be limited to: contacting the bone with a graded series of dehydrating liquids; contacting the bone with dehydrating liquid in the presence or absence of a desiccant, e.g., molecular sieve, anhydrous calcium chloride, anhydrous silica gel, etc.; subjecting the bone to microwave energy such as described in U.S. Pat. No. 4,656,047 the contents of which are incorporated by reference herein; subjecting the bone to heat at ambient or sub-atmospheric pressures, e.g., drying oven at temperatures from about 35° C. to about 85° C., preferably about 40° C. to about 50° C., or vacuum oven at temperatures from about 35° C. to about 85° C., preferably about 40° C. to about 50° C.; subjecting the bone to sub— atmospheric pressure in the presence or absence of a desiccant, e.g., closed container subjected to vacuum optionally containing a desiccant such as anhydrous calcium chloride, anhydrous silica gel or the like; subjecting the bone to ambient temperatures at ambient or sub-atmospheric pressures such as typically found in a laboratory bench-top or conventional fume hood; alternative lyophilization procedures such as starting the lyophilization cycle at a higher temperature to dehydrate the tissue then reducing the temperature and pressure to freeze the tissue and sublimate any remaining moisture as described in Balderson, et al., *The effects of freeze-drying on the mechanical properties of human cortical bone,* 45th Annual Meeting of the Orthopaedic Research Society, : 785, (1999), the contents of which are incorporated by reference herein; or by a combination of one or more of the foregoing. It will be understood that all references to vacuum herein, unless otherwise specified, refer to vacuum pressures as are usually provide by standard sources of laboratory vacuum, e.g., vacuum pump, air-water venturi device, etc.

The monolithic bone treated in accordance with the invention will exhibit a level of toughness which is at least about 5%, preferably at least about 10%, and more preferably at least about 15% greater than that of a comparable specimen of monolithic bone which has been lyophilized. In addition, bone dehydrated according to the invention herein demonstrates at least about 2% less decrease in length dimension as compared to bone that has been lyophilized. At this point, the bone can optionally be further shaped prior to packaging.

There are a variety of conditions by which dehydrated bone can be rehydrated prior to implantation. Soaking the dehydrated bone in rehydrating solution at normal atmospheric pressure can perform rehydration. Alternatively, the dehydrated bone can be rehydrated in a low atmospheric pressure environment, for example, the rehydration solution can be introduced via hypodermic needle through the sealed rubber stopper.

The rehydration solution can be any of a number of suitable agents such as sterile water, normal saline, physiologically buffered saline, dextrose solution, antibiotic solutions, and others of this sort. Optionally, it can contain one or more wetting agents such as any of the Pluronic™ agents or any of a variety of medically/surgically useful substances such as antiviral agents, particularly those effective against HIV and hepatitis; antimicrobials and/or antibiotics such as erythromycin, bacitracin, neomycin, penicillin B, tetracycline, viomycin, chloromycetin and streptomycin, cetazolin, ampicillin, azactam, tobramycin, clindamycin, gentamicin, etc.; amino acids, peptides, vitamins, inorganic elements, co-factors for protein synthesis; hormones; endocrine tissue or tissue fragments; synthesizers; enzymes such as collagenase, peptidases, oxidases, etc.; polymer cell scaffolds with parenchymal cells; angiogenic drugs and polymeric carriers containing such drugs; antigenic agents; cytoskeletal agents; bone morphogenic proteins (BMPs), transforming growth factor (TGF-beta), insulin-like growth factor (IGF-1); insulin-like growth factor two (IGF-2); platelet derived growth factor (PDGF), growth hormones such as somatotropin, etc.

The rehydrated monolithic bone prepared according to the method herein is intended to be applied at a bone defect site, e.g., one resulting from injury, defect brought about during the course of surgery, infection, malignancy or developmental malformation. The bone, suitably sized and shaped as required, can be utilized as a graft or replacement in a wide variety of orthopedic, neurosurgical and oral and maxillofacial surgical procedures such as the repair of simple and compound fractures and nonunions, external and internal fixations, joint reconstruction such as arthrodesis, general arthroplasty, cup arthroplasty of the hip, femoral and humeral head replacement, femoral head surface replacement and total joint replacement, repairs of the vertebral column including spinal fusion and internal fixation, tumor surgery, e.g., deficit filling, discectomy, laminectomy, excision of spinal cord tumors, anterior cervical and thoracic operations, repair of spinal injuries, scoliosis, lordosis and kyphosis method of dehydrating monolithic bones, intermaxillary fixation of fractures, mentoplasty, temporomandibular joint replacement, alveolar ridge augmentation and reconstruction, onlay bone grafts, implant placement and revision, sinus lifts, etc. Specific bones which can be repaired with the bone-derived implant herein include the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal and metatarsal bones.

The invention will be more fully understood by way of the following examples which are intended to illustrate but not limit methods in accordance with the present invention.

Example 1

The samples of the monolithic bone of FIG. 1 where obtained utilizing the same donor material. Initial measurements of 6 sites were determined.

The samples were then processed to dehydrate in a VIP™ tissue processor according to the conditions given in Table 1 below.

TABLE 1

| Step | Concentration | Time (hours) | Temperature (° C.) |
|---|---|---|---|
| 1 | Ethanol | 70% | 4:00 | 45 |
| 2 | Ethanol | 70% | 4:00 | 45 |
| 3 | Ethanol | 95% | 4:00 | 45 |
| 4 | Ethanol | 95% | 4:00 | 45 |
| 5 | Flex 100 | 100% | 4:00 | 45 |
| 6 | Flex 100 | 100% | 4:00 | 45 |

After processing, the specimens were removed from the VIP™ processor and placed in a closed container under continuous vacuum for about 4 hours to outgas any remaining solvent.

Another specimen was treated using the process of Table 1. At the end of the process, the specimen was allowed to outgas for 4 hours 20 minutes in a vacuum dessicator. The specimen was weighed to 0.0001 grams.

In order to determine the level of dessication, the specimen was then placed in a lyophilization unit overnight to remove any remaining water from the specimen. After removal from the lyophilization unit, the specimen was again weighed. The difference indicated a water content of 3.45% water by weight for the alcohol-treated specimen.

After being rehydrated for about 5 minutes, the specimens were again measured to determine the existence of any dimensional changes. The results of this measurement are given in Table 2 below. The percentage change in dimension was determined by calculating the difference between the pre-rehydration dimension and the initial dimension divided by the initial dimension and multiplied by 100. Therefore, all values are in percentage units relative to the initial dimension.

TABLE 2

|  | Anterior Height | Posterior Height | Slot Width | Slot Height | Anterior/ Posterior Diameter | Medial/ Lateral Diameter |
|---|---|---|---|---|---|---|
| Alcohol Only |  |  |  |  |  |  |
| Specimen 1 | −0.67 | −0.46 | −1.78 | −1.03 | −0.59 | −0.28 |
| Specimen 2 | −1.13 | −0.31 | −0.54 | −2.02 | −0.84 | −0.71 |
| Avg. | −0.90 | −0.39 | −1.16 | −1.53 | −0.71 | −0.49 |
| S.D. | 0.33 | 1.11 | 0.88 | 0.70 | 0.18 | 0.31 |
| Freeze-Dry |  |  |  |  |  |  |
| Specimen 3 | −5.40 | −1.60 | −2.12 | −9.50 | −3.70 | −2.43 |
| Specimen 4 | −2.40 | −1.45 | −0.54 | −7.11 | −2.11 | −2.41 |
| Specimen 6 | −1.97 | −1.94 | −1.79 | −6.57 | −2.36 | −3.03 |
| Avg | −2.13 | −1.41 | −1.29 | −7.17 | −2.87 | −2.16 |
| SD | 2.72 | 0.55 | 0.78 | 1.68 | 0.76 | 0.96 |

Comparative Example 1

Samples of the monolithic bone of FIG. 1 were obtained from three different donors. The bone was then either processed according to the procedure of Example 1 with five minutes or two hours of hydration time, lyophilized under industry standard conditions or frozen. The samples were then subjected to compression to breakage using a uniaxial servo-hydraulic test machine (MTS model 858 Bionix) under displacement control to apply a constant compressive displacement to each test articles at a rate of 25 mm/min. Before the start of each test, a compressive preload was applied to each specimen (under load control) of 250N and machine displacement was zeroed at this point. This was done to provide a consistent zero displacement starting point for each test. Tests terminated when a total compressive displacement of 2.5 mm had been imparted to the test article. In all cases, failure (a peak in load, followed by a sharp drop in load) was observed before 2.5 mm of compressive displacement was reached. Test articles were loaded using stainless steel inserts which conformed to the upper and lower ridged surfaces of the test article, with the exception of two small mounting holes on both the lower and upper insert. The system 100 kN load cell in the 100 kN range was used to collect load information. Displacement information was measured from the test systems displacement transducer (LVDT). Peak loads and energy to break values were extracted from the load vs. displacement curves using Testworks version 3.6 test software.

Measurements of the breaking energy values was determined as an indicator of toughness. The results are contained in Table 3 below. All units are in N-mm.

TABLE 3

|  | Frozen | Freeze-Dried (5 minute rehydration) | Alcohol (5 min rehydration) | Alcohol (2 hour rehydration) |
|---|---|---|---|---|
| Donor 1 | 39731 | 24638 | 31587 | 41004 |
| Donor 2 | 29546 | 24425 | 18078 | 27142 |
| Donor 3 | 25531 | 22038 | 24122 | 19222 |
| Donor 4 | 24534 | 13924 | 25926 | N/A |
| Average | 29835 | 21256 | 24928 | 29122 |
| Standard Deviation | 6943 | 5028 | 5565 | 11025 |
| Percentage Relative to Frozen | 100% | 71.2% | 83.6% | 97.6% |
| Percentage relative to lyophilized (freeze-dried) bone | 140.4% | 100% | 117.3% | 137.0% |

After being subjected to compression to fracture, the monolithic bone was visually evaluated to determine the relative degree of fragmentation of each treatment method. This relative degree of fragmentation is also an indicator of toughness. The degree of fragmentation of the monolithic bone was scored on a relative scale from 1 to 10 wherein 1 represented no fragmentation and 10 represented highly fragmented. The results are contained in Table 4 below.

TABLE 4

|  | Frozen | Freeze-Dried (5 minute rehydration) | Alcohol (5 min rehydration) | Alcohol (2 hour rehydration) |
|---|---|---|---|---|
| Donor 1 | 2 | 6 | 2 | 2 |
| Donor 2 | 2 | 7 | 4 | 2 |
| Donor 3 | 2 | 4 | 2 | 2 |
| Donor 4 | 2 | 7 | 4 | N/A |
| Average | 2 | 6 | 3 | 2 |

From this above data, two separate measures of energy absorption indicate that freeze-drying decreases toughness. Alcohol treatment also decreases toughness, but by less than for a comparable freeze-dried graft (29% reduction for FD vs. 16% reduction for alcohol). The may be very significant at the time of graft insertion, since many of the grafts that would receive this treatment will receive mechanical blows (hammering, etc.) to place them in the surgical site. At later time points, after rehydration for 2 hours (whether in a container in the operating room, or rehydrating in the patient's surgical site), the graft behaves similarly to the frozen tissue in its toughness characteristics.

It will be understood that various modifications can be made to the embodiments and examples disclosed herein. Accordingly, the above description should not be construed as limiting but merely exemplary of preferred embodiments. Those skilled in the art will envision such various modifications that are within the scope of the claims appended.

What is claimed is:

1. A method for dehydrating monolithic bone intended for implantation to conserve toughness of the bone during dehydration and subsequent packaging and maintain such toughness during storage of the bone, the method comprising: dehydrating the monolithic bone to less than about 6 percent water content wherein dehydrating the monolithic bone consists of contacting the bone with at least one biocompatible dehydrating liquid and controlling pressure surrounding the monolithic bone during such contact; removing the dehydrating liquid; and packaging the dehydrated bone, wherein dehydrating the monolithic bone to less than about 6 percent water content is accomplished without lyophilizing, freeze drying, or oven drying the bone and wherein the conserved bone toughness is at least about 10% greater than that of a comparable specimen of monolithic bone which has been lyophilized.

2. The method of claim 1 wherein contacting the bone with at least one biocompatible dehydrating liquid and controlling pressure during such contact comprises infusing the dehydrating liquid under pressure.

3. The method of claim 1 wherein contacting the bone with at least one biocompatible dehydrating liquid and controlling pressure during such contact comprises infusing the dehydrating liquid under alternating levels of positive pressure.

4. The method of claim 1 wherein contacting the bone with at least one biocompatible dehydrating liquid and controlling pressure surrounding the monolithic bone during such contact comprises contacting the bone with at least one biocompatible dehydrating liquid in the presence of a low pressure atmosphere.

5. The method of claim 1 wherein contacting the bone with at least one biocompatible dehydrating liquid and controlling pressure surrounding the monolithic bone during such contact comprises contacting the bone with at least one biocompatible dehydrating liquid in the presence of alternating vacuum and positive pressure.

6. The method of claim 1 wherein the dehydrating liquid is selected from the group consisting of methanol, ethanol, isopropanol, butanol, isobutanol, ethylbutanol, acetonitrile, pyridine, industrial methylated spirit, graded series of dehydrating agents, histological solution, Flex 1 OO™, dimethylsulfoxide, small ketones, acetone, chloroform, methylene chloride, ethylene chloride, straight chain hydrocarbons of less than 12 carbons, hexane, pentane, low molecular weight alkenes, esters, ethers, ethyl ether, tetrahydrofuran, dioxane, ethylene glycol monoethyl ether, crown ethers, aldehyde, solutions containing aldehydes, formaldehyde, formalin, super critical fluids, liquid carbon dioxide, liquid hydrogen sulfide, and mixtures of two or more of the above liquids.

7. The method of claim 1 wherein contacting the bone with at least one biocompatible dehydrating liquid comprises contacting the bone with a graded series of dehydrating liquids.

8. The method of claim 1 wherein removing the dehydrating liquid comprises subjecting the bone to microwave energy.

9. The method of claim 1 wherein controlling pressure comprises subjecting the bone to sub-atmospheric pressure in the absence of a desiccant.

10. The method of claim 1 wherein removing the dehydrating liquid comprises subjecting the bone to ambient temperature at ambient pressure.

11. The method of claim 1 wherein removing the dehydrating liquid comprises subjecting the bone to ambient temperature at sub-atmospheric pressure.

12. The method of claim 1 wherein removing the dehydrating liquid comprises subjecting the bone to heat at ambient pressure.

13. The method of claim 1 wherein removing the dehydrating liquid comprises subjecting the bone to heat at sub-atmospheric pressure.

14. The method of claim 1 wherein removing the dehydrating liquid comprises subjecting the bone to sub-atmospheric pressure in the presence of a desiccant.

15. The method of claim 1 wherein removing the dehydrating liquid comprises subjecting the bone to sub-atmospheric pressure in the absence of a desiccant.

16. The method of claim 1, further comprising, after achieving dehydration of the monolithic bone to less than about 6 percent water content with the dehydrating liquid, further reducing the water content using a second dehydration step.

17. The method of claim 1, wherein the conserved toughness is at least about 15% greater than that of a comparable specimen of monolithic bone which has been lyophilized.

* * * * *